United States Patent [19]

Rehder

[11] 4,271,849
[45] Jun. 9, 1981

[54] APPARATUS FOR PRODUCING RELIEF GROOVES IN PAN-SHAPED BONES

[75] Inventor: Günther Rehder, Stuhr, Fed. Rep. of Germany

[73] Assignee: Orthoplant Orthopadische Implantate GmbH & Co., Bremen, Fed. Rep. of Germany

[21] Appl. No.: 42,808

[22] Filed: May 29, 1979

[30] Foreign Application Priority Data

Aug. 4, 1978 [DE] Fed. Rep. of Germany ....... 2834296

[51] Int. Cl.³ .......................... A61F 5/04; A61F 17/32
[52] U.S. Cl. ............................. 128/92 E; 128/92 EB; 128/305
[58] Field of Search ..................... 128/321, 305, 305.1, 128/304, 310, 312, 317, 92 E, 92 L, 92 LA, 92 B, 92 EB; 30/276, 300, 310; 82/1.2; 408/154, 163, 164, 165, 168, 171

[56] References Cited

U.S. PATENT DOCUMENTS

| 655,600 | 4/1900 | Haddock | 408/154 |
|---|---|---|---|
| 1,278,570 | 7/1918 | Beck | 408/168 |
| 1,281,519 | 3/1918 | Clark | 408/168 |
| 2,472,554 | 9/1949 | Volis | 408/154 |
| 2,694,321 | 6/1954 | Riza | 408/154 |
| 3,200,673 | 6/1965 | Pfeifer | 408/154 |
| 3,246,545 | 7/1966 | Shugars | 408/154 |
| 3,468,312 | 9/1969 | Kuntscher et al. | 128/317 |
| 3,633,583 | 7/1972 | Fishbein | 128/305 |
| 3,702,611 | 11/1972 | Fishbein | 128/305 |

Primary Examiner—Robert W. Michell
Assistant Examiner—C. W. Shedd
Attorney, Agent, or Firm—Toren, McGeady and Stanger

[57] ABSTRACT

Apparatus is disclosed for producing relief grooves in pan-shaped bones, especially in the acetabulum of a human hip joint. The apparatus includes a drivable drive shaft having a free end section. A casing is arranged on the free end section. The casing has an exterior contour which, facing away from the drive shaft is, at most, as large as the pan-contour of the bone. At least one cutting device is arranged in the casing which is movable transversely relative to the longitudinal axis of the drive shaft. The cutting device has a cutting edge arranged in an outwardly radial direction. An adjusting device is included which cooperates with the cutting device. The cutting edge is arranged in an initial position within the casing and is radially movable outwardly by means of the adjusting device.

17 Claims, 3 Drawing Figures

APPARATUS FOR PRODUCING RELIEF GROOVES IN PAN-SHAPED BONES

FIELD OF THE INVENTION

The invention relates to an apparatus for producing relief grooves in pan-shaped bones, especially in the acetabulum of a human hip joint.

BACKGROUND OF THE INVENTION

It is known in bone surgery to frequently replace the natural sliding surfaces of joints with artificial sliding surfaces in cases of certain fractures or diseases relating to wear, e.g., arthrosis.

In the case of the human hip joint, the creation of an artificial acetabulum pan, which usually consists of plastic material, is independent of whether the femur head of the respective hip joint is essentially preserved and only provided with a shell prosthesis, or the femur head is radically removed and a suitable metal part which also has, inter alia, an artificial femur head, is substituted therefor.

The creation of artificial joint pans has the disadvantage that they must be fixed with bone cement after a cutting of the natural pan. Usually there must be used a considerable amount of bone cement, because the bone tissues often are not specially compatible with such bone cement, so that a formation of spongiosis and loosening of the hip pan can occur.

Therefore, it would be advantageous if such artificial joint pans could be fixed in a form-locking manner on the respective bone. Unfortunately, this has been impossible thus far, because it was not possible to exactly produce the respective recesses in the tissue. With respect to the exactness of such recesses, which are suitable and intended for holding artificial joint pans in a form-locking manner, relatively high demands must be made as to the accuracy of fit.

This difficulty was considered even greater, because such recesses grip the pan edge from behind in order to hold any projections of artificial joint pans, and must have a sufficiently large distance to the natural pan edge to keep the occurring loads sufficiently small.

SUMMARY OF THE INVENTION

Thus, an object of the present invention is to create an apparatus of the type described with which such recesses can be made in the form of relief grooves in pan-shaped bones, especially in the acetabulum of a human hip joint, without using any or, at most, a small amount of bone cement.

The solution of this object resides, according to the invention, in an apparatus which comprises a drivable drive shaft, on whose free end section there is arranged a casing whose exterior contour, which is facing away from the drive shaft, is, at most, as large as the pan contour. Furthermore, in the casing, at least one cutting means is arranged which is movable transversely relative to the longitudinal axis of the drive shaft and whose cutting edge, located radially outwardly, is arranged in the initial position within the casing, and is movable radially outwardly by means of an adjusting device.

For a better understanding of the present invention, reference is made to the following description and accompanying drawings, while the scope of the present invention will be pointed out in the appended claims.

DESCRIPTION OF THE PREFERRED EMBODIMENT

Figure 1:
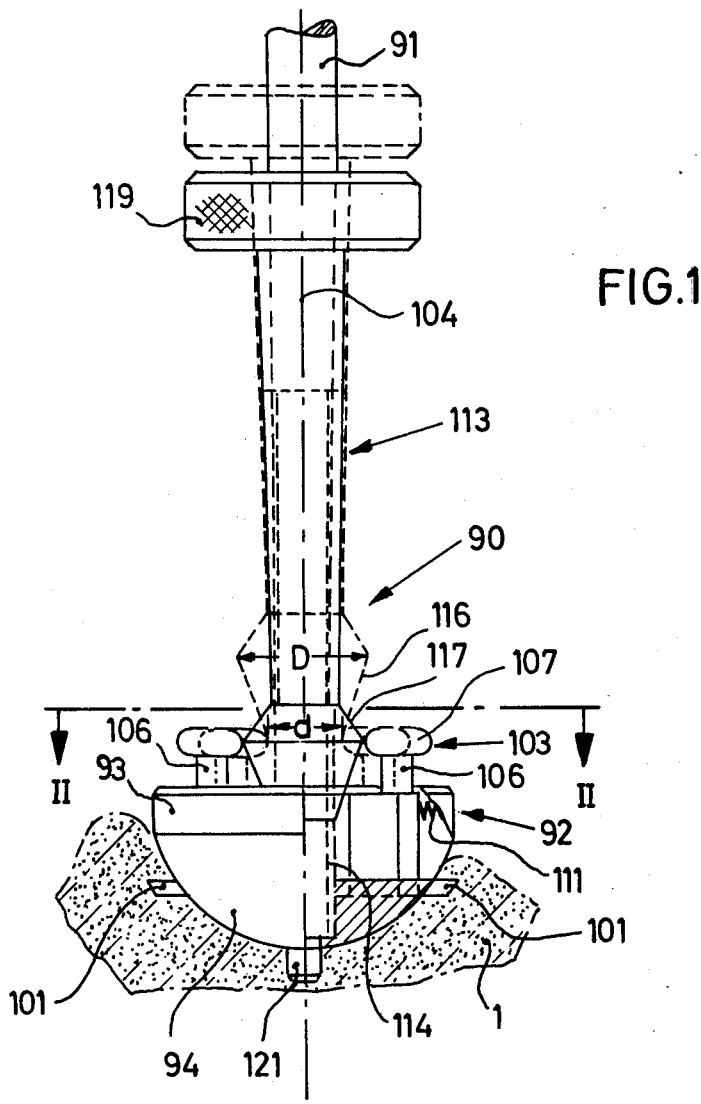
FIG. 1 shows a side view of the apparatus according to the invention, during the end of the cutting procedure, partially in section.
Figure 3:
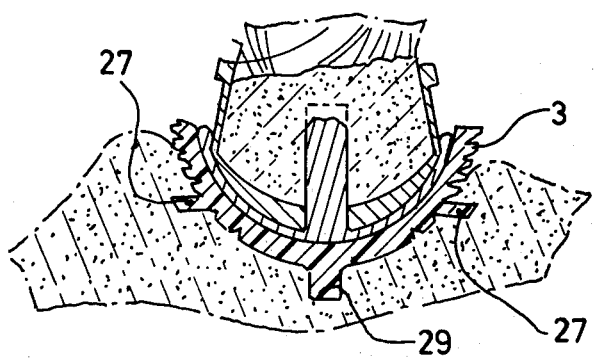
FIG. 3 shows the acetabulum, as seen in section in FIG. 1, after finished treatment, having an inserted implant.
Figure 2:
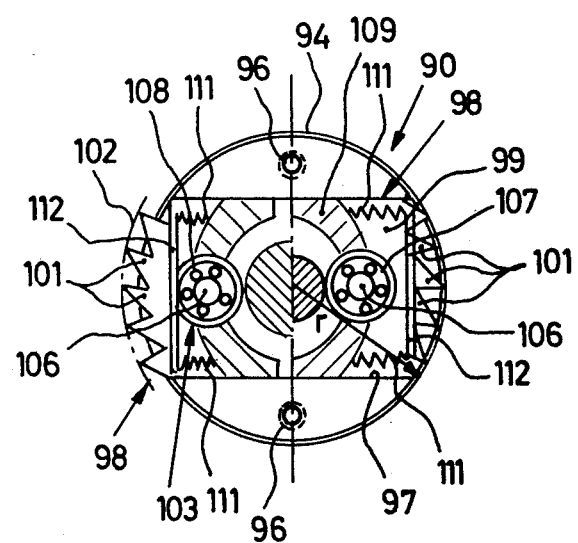
FIG. 2 shows a top view of the apparatus according to FIG. 1 in the direction of line II—II, wherein the casing cover is removed.

The apparatus 90 shown in FIGS. 1 and 2 for producing relief grooves in pan-shaped bones is illustrated and described with relation to a development and use for the creation of a groove in the acetabulum 1 of a human hip joint.

The apparatus 90 has a drive shaft 91 which is drivable by a drive mechanism, not shown. On the free end section of the drive shaft 91, there is arranged a casing 92. The casing 92 has a lower end surface which is of spherical shape. The upper surface of the casing is covered by a removable cover 93 which is fixed to the lower part 94 of the casing 92 by screws which are not shown for the sake of clarity. The mentioned screws are screwed into tapped holes 96 of the lower part 94.

As can be seen especially from FIG. 2 the lower part 94 of the casing 92 is provided on its upper surface with a symmetrical guide, constructed as a slot or groove 97. This guide extends from the center towards the outer edge. The groove-shaped guide 97 serves for guiding two diametrically opposed cutting means 98 which are mirror-symmetrical with respect to each other. Each of the cutting means 98 is composed of a base plate 99 on whose outer rim, the cutting edge is constructed in the shape of cutting teeth 101. The cutting teeth 101 are located on an arc of a circle 102 whose radius r corresponds to the casing radius on the outlet point of the cutting teeth 101.

Each of the cutting means 98 has a guiding head 103 which cooperates with an adjusting device as will be described further below. The guiding head 103 consists of a pin 106 which protrudes from the base plate 99 and is parallel to the longitudinal axis 104 of the drive shaft 91. On the free end of the pin, there is arranged a guiding roller 107 which is mounted on the pin 106, so as to be rotatably movable, but axially immovable, through a ball bearing 108.

Each of the pins 106 is fixed in a collar 109 which protrudes from the base plate 99 of the cutting means 98.

Each of the cutting means 98 is mounted in the casing against the restoring force of two springs 111. These springs are coil springs and are arranged parallel to each other and spaced apart, wherein both springs 111 of each cutting means 98 are connected to each other through a stirrup 112. Each of the springs is supported on its one end on the collar 109 of the respective cutting means 98, and on its other end on the stirrup 112, wherein the stirrup 112 is supported by the cover 93 of the casing 92.

The adjusting device has an adjusting bush 113 which is arranged concentrically on the drive shaft 91 and is connected with the drive shaft 91 through a fine thread 114.

The diameter d of the lower end section of the adjusting bush 113 has a dimension such that the cutting means 98 is still located completely in the casing 92 during fitting of the guiding head 103 on the lower end section of the adjusting bush 113.

Above the smallest diameter d of the adjusting bush 113, there is a first conical section 116 whose largest diameter D is of such a size that the cutting teeth 101 are completely radially extended during fitting of the respective guiding head 103, as can be seen in the portion of FIG. 1 with solid lines and in FIG. 2 in the left part of the drawing. The right part of the illustration according to FIG. 2 shows the above-mentioned stage in which the cutting teeth 101 are still completely in the casing. Adjacent to and directly above this first conical section 116 is a second conical section 117 with decreasing diameter whose smallest diameter, at the upper end, is approximately of the same size as the smallest diameter d of the first conical section 116.

On the upper end of the adjusting bush 113, there is an adjusting flange 118 whose outer jacket 119 is provided with knurling for roughing and the creation of a better grip.

The mode of operation of the apparatus shown in the drawings and above described, is as follows:

After the acetabulum 1 has been cut with a spherical shell-end mill in a mainly uniform shape of a spherical indentation, and a centering bore for a centering pin 121 arranged on the outer side of the casing 92 has been provided in the tissue, the apparatus 90 is set in the position with retracted cutting means 98 (in FIG. 1 with dash-dotted illustration and in FIG. 2, the right portion). When the drive shaft 91 is then rotated about its longitudinal axis 104, wherein the hand of the operating surgeon does not act on the adjusting flange 118, the above-described stage initially is maintained.

Only when the operating surgeon acts with his hand on the jacket 119 of the adjusting flange 118 and moves the adjusting bush 113 downwardly relative to the drive shaft 91 by way of the thread connection 114 between the adjusting bush 113 and the drive shaft 91 does the guiding rollers 107 of the guiding heads 103 start to move upwardly along the first conical section 116. Thus, the guiding heads 103 with their pins 106 and cutting means 98, which are fixed thereon, are radially moved outwardly against the force of the springs 111 so that the cutting teeth 101 move radially outwardly out of the casing 92 and begin to cut into the bone tissue.

The operating surgeon, who can interrupt this adjusting procedure at any time in a most simple manner by releasing the adjusting flange 118, performs this procedure as long as the guiding heads 103 have reached and exceeded the largest diameter D of the first and second conical section 116 and 117. The guiding heads 103 then go back to approximately a diameter d along the second conical section 117, so that the cutting teeth 101 are located again completely within the casing 92 at the end of the treatment procedure.

Then, the apparatus 90 can be removed from the acetabulum 1 without any trouble because there is no need of a separate step for retracting of the cutting means 98. After the treatment procedure, the acetabulum 1 is provided with a groove-shaped recess which corresponds to the completely extracted position of the cutting teeth 101, as can be seen by the solid lines in FIG. 1.

Subsequently, there can be inserted in the acetabulum 1, in form-locking manner, an acetabulum pan 3 which is composed of a plastic material and is provided with tongue-shaped projections 27. Because of their elasticity, the projections 27 bend at first during the insertion, and then snap into the previously created groove. The centering bore for the centering pin 121 is filled in by a centering pin 29 which is integrally connected with the acetabulum pan.

Such an application needs obviously no bone cement. In any case, at most, an extremely small amount of bone cement is sufficient so that the above-mentioned disadvantages do not occur. The above advantages can be achieved, although only extremely little tissue material needs to be removed, since the groove for the projection 27 can be provided at a location low enough to prevent an excessive stress of the acetabulum rim.

As has been described above, the casing of the present invention is preferably constructed symmetrically with respect to rotation and suitably has a spherical shape. Thus, a specially good adjustment of the apparatus to the pan is possible when the pan has previously been treated with a correspondingly shaped shell-end mill. A good adjustment is particularly possible, when the pan is previously cut, not only in the shape of a spherical identation, but also to include a central bore, in which a centering pin can be inserted. The centering pin extends centrally from the exterior surface of the casing to the outside.

The cutting means is radially guided in the casing, preferably by means of a guide which can be constructed as a slot or groove extending from the center of the casing towards the exterior surfaces.

Such a development is especially then suitable when the cutting means is constructed in the shape of a plate, at whose edge, located on the outside, the cutting edge is constructed in the shape of cutting teeth.

Further, in such a development, the cutting teeth are preferably arranged on an arc of a circle whose radius corresponds to the casing radius on the emergence point of the cutting teeth out of the casing.

In order to perform the radially outward movement of the cutting means in an optimum way, each of these cutting means has a guiding head cooperating with the adjusting device which is described further below. The guiding head can consist of a pin, which is arranged parallel to the longitudinal axis of the drive shaft and extends upwardly from the plate-shaped cutting means. On the free end of the pin, there is arranged a guiding roller which is preferably mounted rotatably, but is axially immovably on the pin through a bearing, for example, a ball bearing.

Each of the cutting means is preferably mounted in the casing against the restoring force of at least one spring. However, two parallel springs having distance therebetween arranged between the casing and each of the cutting means are also suitable. The springs can be coil springs and can be connected by means of a spacer clamp or stirrup, or the like.

The interchangeability of the cutting means which is achievable with the apparatus according to the invention, is especially important because a regrinding of the cutting edges cannot be performed in view of the necessary dimensional accuracy. If the cutting teeth are reground and respective material is removed from them, the relief groove which is produced by the cutting teeth afterwards would have a smaller exterior diameter than before the regrinding so that a respective artificial hip pan with corresponding tongue-shaped lugs would not fit anymore into the pan.

The adjusting device preferably is composed essentially of an adjusting bush, arranged concentrically on the drive shaft and connected with the drive shaft through a thread which is suitably a fine thread in order to obtain a sensitive feed motion or adjustment.

As further discussed above, the adjusting bush has on its lower end section a diameter which is, at most, of such a size that the cutting means is still completely located within the casing during fitting of its guiding head on the lower end section of the adjusting bush. In this position, no cutting procedure can take place and, therefore, the tissue of the bone pan cannot be damaged during positioning.

Furthermore, the adjusting bush has preferably a first section which extends upwardly and whose diameter increases, wherein its largest diameter is of such a size that the cutting means protrudes completely radially from the casing when its guiding head rests on this largest diameter.

Adjacent to and above the first section of the adjusting bush, there is preferably a second section whose diameter decreases, wherein its smallest diameter located on the upper end is approximately of the same size as the smallest diameter of the first section.

The first section, as well as the second section of the adjusting bush is preferably conically constructed, so that a constant and uniform increase of the cutting radius is achieved when the adjusting device is actuated as has been described.

The adjusting bush has on its upper end section preferably an adjusting flange on which the hand of the operating surgeon can selectively act, in order to move the cutting means radially outwardly.

While the foregoing description and drawings represent the preferred embodiments of the present invention, it will be obvious to those skilled in the art that various changes and modifications may be made therein without departing from the true spirit and scope of the present invention.

LIST OF REFERENCE NUMERALS

1—Acetabulum
3—Acetabulum pan
27—Projections
29—Centering pin
90—Apparatus
91—Drive shaft
92—Casing
93—Removable Cover
94—Lower part
96—Tap bores
97—Groove
98—Cutting means
99—Base plate
101—Cutting teeth
102—Arc of a circle
103—Guiding head
104—Longitudinal axis
106—Pin
107—Guiding roller
108—Bearing
109—Collar
111—Springs
112—Clamp
113—Adjusting bush
114—Thread
116—First conical section
117—Second conical section
118—Adjusting flange
119—Jacket
121—Centering pin

What is claimed is:

1. Apparatus for producing relief grooves in a pan-shaped bone such as the acetabulum of a human hip joint, comprising:
   an elongated drive shaft having a free end;
   a casing arranged at the free end of said drive shaft, said casing having an outside contour of generally hemispherical shape facing away from said drive shaft and which shape is at most coextensive with the pan contour of the bone;
   cutting means arranged in said casing for movement transversely of the longitudinal axis of said drive shaft, said cutting means having a cutting edge which is movable between a first position inside said casing and a second position outside said casing in a radial direction relative to the longitudinal axis of said drive shaft, said casing having passageways to allow said cutting edge to emerge from said casing toward the second position; and
   an adjusting bush threadably connected to and arranged concentrically on said drive shaft for radially moving said cutting means, said adjusting bush including a first section having an increasing outer diameter and a second, successively connected section have a decreasing outer diameter in the direction of the longitudinal axis of said drive shaft, the outer circumferential surfaces of said first and said second sections operatively engaging said cutting means.

2. Apparatus according to claim 1, wherein said passageways form a groove for guiding said cutting means in the radial direction relative to the longitudinal axis of said drive shaft.

3. Apparatus according to claims 1 or 2, wherein said cutting means includes a plate arranged transversely of the longitudinal axis of said drive shaft, and said cutting edge includes cutting teeth arranged at the radially outer periphery of said plate.

4. Apparatus according to claim 3, wherein said cutting teeth are located on an arc of a circle whose radius corresponds to the radius of said casing at the location thereon where said cutting teeth emerge from said casing when said cutting edge moves toward the second position.

5. Apparatus according to claim 3, wherein said cutting means includes a guiding head for contacting said adjusting bush.

6. Apparatus according to claim 5, wherein said guiding head comprises a pin protruding from said plate in a direction toward and parallel to the longitudinal axis of said drive shaft, and a guiding roller arranged at the free end of said pin.

7. Apparatus according to claim 6, including a bearing for holding said guiding roller on said pin for rotation about the axis of said pin and for fixing said guiding roller against axial movement relative to the axis of said pin.

8. Apparatus according to claim 5, including a removably mounted cover attached to the end of said casing which faces toward said drive shaft, said cover having an opening for passage of said first and said second sections of said adjusting bush.

9. Apparatus according to claim 8, wherein said guiding head is arranged to extend from said cover toward said drive shaft.

10. Apparatus according to claim 3, including at least one spring for applying a restoring force to said cutting means for holding said cutting means in said casing.

11. Apparatus according to claim 10, including two spaced apart coil springs arranged between said casing and said cutting means.

12. Apparatus according to claim 11, including a clamp for connecting said two springs.

13. Apparatus according to claim 1, wherein said cutting means is arranged to be exchangeable.

14. Apparatus according to claim 1, wherein said cutting means includes two cutting members which are located opposite each other in a radial direction relative to the longitudinal axis of said drive shaft.

15. Apparatus according to claim 1, wherein said first and said second sections of said adjusting bush are constructed together in the form of two frusto-conical surfaces.

16. Apparatus according to claim 1, including an adjusting flange at the end of said adjusting bush which end faces away from said casing.

17. Apparatus according to claim 1, including a centering pin protruding centrally from the outside surface of said casing away from said drive shaft in the direction of the longitudinal axis of said drive shaft for engaging a center bore provided in the bone.

* * * * *